United States Patent [19]

Soll et al.

[11] Patent Number: 4,971,955
[45] Date of Patent: Nov. 20, 1990

[54] PROTECTION OF HUMAN AND ANIMAL CELLS DURING SURGICAL TRAUMA

[76] Inventors: David B. Soll, David B. Soll, M.D. Associates, 5001 Frankford Ave., Philadelphia, Pa. 19124; Sol E. Harrison, 1627 Buck Hill Dr., Huntingdon Valley, Pa. 19006

[21] Appl. No.: 162,940

[22] Filed: Mar. 2, 1988

Related U.S. Application Data

[60] Division of Ser. No. 677,130, Dec. 3, 1984, abandoned, which is a continuation-in-part of Ser. No. 239,791, Mar. 2, 1981, Pat. No. 4,486,416.

[51] Int. Cl.$^5$ .......................................... A61K 31/715
[52] U.S. Cl. ................................................. 514/54
[58] Field of Search ........................ 435/240.2; 514/54

[56] References Cited

U.S. PATENT DOCUMENTS 1,950,100  3/1934  Crandall ................................. 514/54
4,105,760  8/1978  Szejtli et al. .......................... 514/54
4,640,912  2/1987  Hausman .

OTHER PUBLICATIONS

*Webster's II New Riverside Dictionary*, p. 562 (Boston; Houghton Mifflin Company, 1984).

Morii et al.—Chem. Abst. vol. 72 (1970) p. 35780t.
Cheng—Chem. Abst. vol. 103 (1985) p. 189,544q.
Morrison et al.—Chem. Abst. vol. 63 (1965) p. 12090g.
Wolarsky et al.—Chem. Abst. vol. 63 (1965) p. 18766e.

*Primary Examiner*—Sam Rosen
*Attorney, Agent, or Firm*—Panitch Schwarz Jacobs & Nadel

[57] ABSTRACT

The cells of the coverings and linings of internal human and animal tissues, organs and body cavities subject to trauma, such as surgery, may be protected against exfoliation or destruction by the topical application or injection of effective amounts of chondroitin sulfate prior to or during the trauma. Preferably, the chondroitin sulfate is used in physiological solutions in concentrations of about 40 to 55 weight percent, and may be used as a surgical irrigating solution. Intraarticular injection of such chondroitin sulfate solutions into human and animal joints having degenerative joint conditions protects the joint cells, reduces aseptic inflammation and/or prevents further dengeration of cartilage tissue. Solutions for preserving human and animal cells and tissues in vitro for later in vivo use have extended storage life when chondroitin sulfate is added to such storage solutions in effective amounts such as about 1 to 20 weight percent of the storage solution.

11 Claims, No Drawings

PROTECTION OF HUMAN AND ANIMAL CELLS DURING SURGICAL TRAUMA

This is a divisional application of copending U.S. patent application Ser. No. 677,130, filed Dec. 3, 1984, now abandoned which is a continuation-in-part of U.S. patent application Ser. No. 239,791, filed Mar. 2, 1981, now U.S. Pat. No. 4,486,416, entitled "Protection of Human and Animal Cells Subject to Exposure to Trauma."

This invention relates to a method of protecting both human and animal cells which are subject to exposure to trauma. A particularly important embodiment of this invention concerns using chondroitin sulfate to protect cells in anticipation of surgical trauma.

BACKGROUND OF THE INVENTION

The therapeutic qualities of hyaluronic acid to aid wound healing have been previously reported by E. A. Balasz and D. A. Gibbs in "The Rheological Properties and Biological Function of Hyaluronic Acid", Academic Press (New York), 1970. Ultrapure hyaluronic acid and the use thereof is the subject of U.S. Pat. No. 4,141,973 to E. A. Balazs. Furthermore, it has been shown that sulfated mucopolysaccharides have a greater deturgescence effect on the cornea and that viable corneal stroma incorporate sulphur from a bath containing sulfate. See M. E. Langham, "Macromolecular Organization Of A Connective Tissue", Johns Hopkins Press, 1968; J. A. Capella, H. F. Edelhauser, D. L. Van Horn, "Corneal Preservation", Charles C. Thomas Publisher, 1973.

U.S. Pat. No. 3,211,616 of Zensaku Yosizawa concerns N,O-sulfated neutral-mucopolysaccharides.

U.S. Pat. No. 1,950,100 of Lathan A. Crandall relates to chondroitin compounds and their preparation. Crandall discloses that chondroitin is suitable for the treatment of such diseases as migraine, urticarial eruptions, peptic ulcers, multiple sclerosis, allergies and hepatic cirrhosis.

It is known that chondroitin sulfates are effective in preventing the development and evolution of some types of complicated lesions in atherosclerosis. Also the chondroitin sulfates exhibit a marked increase during reparative processes which ensue after various injuries.

SUMMARY OF THE INVENTION

There has now been discovered a method to protect both human and animal cell layers and tissues subject to exposure to trauma. This method involves administering a prophylactically effective amount of chondroitin sulfate to the anticipated site of the trauma (to the cells and tissues) prior to and/or during exposure to the trauma. Administration of an effective dosage of chondroitin sulfate is particularly useful to prevent cell damage during surgery and trauma such as may occur to a joint surface. Additionally, chondroitin sulfate which is a known agent for promoting wound healing, can be administered after trauma as an aid in healing.

The present invention is particularly directed to protection of the cells of the coverings and linings of all internal body cavities and organs, such as endothelial cells which line the blood vessels and other organs, mesothelial cells which line the abdomen and pleural cavities and epithelial cells which line the esophagus and mouth. According to the invention, chondroitin sulfate is particularly useful as an irrigating solution during surgery in order to prevent cell damage and subsequent adhesion formation.

Chondroitin sulfate may also be added to conventional or special tissue storage solutions to increase the time during which animal tissues or organs may be stored or shipped. Such storage solutions having improved storage time may contain an effective amount of chondroitin sulfate together with the usual metal ions and other nutrients necessary for storage of animal tissues.

Still further, chondroitin sulfate has been found to be effective in ameliorating aseptic joint inflammation in the knees, hips, feet and other joints of animals, particularly four-legged animals such as horses. The chondroitin sulfate reduces the inflammation of the joint and protects the surfaces and cells of the joint tissues from further damage and deterioration.

DETAILED DESCRIPTION OF THE INVENTION

Animal connective tissues contain a group of closely related acidic carbohydrate polymers which are located in the extracellular matrix and are collectively known as mucopolysaccharides. Mucopolysaccharides are heteropolysaccharides formed by the chain condensation of a pair of monomeric sugar units in an alternating sequence, and as a result, these large polymers are invariably built-up from disaccharide repeating units. One of the monomers of mucopolysaccharides is always a hexosamine (2-amino-2-deoxyglycose). The basic amino group of the hexosamine is always present as the neutral acetamino derivative.

Chondroitin sulfate has three isomers (chondroitin sulfate A, chondroitin sulfate B and chondroitin sulfate C) that are characterized by a sulfate group taking one of three positions in the repeating disaccharide unit (N-acetylchondrosin is the repeating unit). Each repeating disaccharide unit has one sulfate group. See The Merck Index, monograph 2194, pages 314–315 (10th ed. 1983).

Chondroitin sulfates A and C both contain D-glucuronic acid, 2 amino-2 deoxy-D-galactose, acetyl and sulfate residues in equimolar quantities. There is a close similarity in structure between chondroitin sulfates A and C, demonstrated by the fact that both afford the same disaccharide, chondrosine, in high yields on acidic hydrolysis. These two mucopolysaccharides are distinguished by their optical rotation and by the solubility of their calcium salts in aqueous ethanol. Chondroitin sulfates A and C structurally differ only in the position of the sulfate ester grouping in the hexosamine residue; the sulfate ester occurs at carbon-4 in the chondroitin sulfate A and carbon-6 in the chondroitin sulfate C. The nature of the hexuronic acid (L-iduronic acid) of chondroitin sulfate B serves to distinguish it from other isomeric chondroitin sulfates.

The similarity of the carbon skeleton in chondroitin sulfate B to that of chondroitin sulfate A and C is evident. In all three acid mucopolysaccharides the acid linkage is BI-3 the hexosaminidic linkage is BI-4 and the hexosamine is galactosamine.

The assignment of sulfate ester groups in chondroitin sulfates A and C to carbon-4 and carbon-6 respectively was initially based upon infrared spectral analysis, since equatorially and axially-located sulfate groups absorb at different wave lengths in the region 700–1000 cm-1. Methylation studies have confirmed this assignment in chondroitin sulfate A.

Chondroitin sulfate B is not degraded by pneumoccal or testicular hyaluronidases and can, therefore, be distinguished from hyaluronic acid and chondroitin sulfates A and C because of this action. Its negative optical rotation ($\alpha_D = -55$ degrees to $-63$ degrees) is much greater than that of chondroitin sulfate A ($\alpha_D = -28$ degrees to $-33$ degrees) or chondroitin sulfate C ($\alpha_D = -16$ degrees to $-22$ degrees).

Chondroitin sulfate is a sulfate acid mucopolysaccharide, which is a normal component of human cornea, and is ubiquitous in animal tissue. It is a viscous substance that has a molecular weight of about 50,000 to 100,000 depending on the source, although lower molecular weight species on the order of about 20,000 to 50,000 are also sometimes present. Chondroitin sulfate is effective in the present invention at all molecular weights.

The sulfate ester content of the chondroitin sulfates is subject to wide variations depending on the source. The sulfate ester content of chondroitin sulfates in corneal extracts is usually consistently low. In contrast, the sulfate ester content of chondroitin sulfates obtained from shark connective tissues is high when compared to the sulfate ester content of chondroitin sulfates derived from equivalent mammalian sources. The degree of sulphation is not believed to have any significance in the applicability of chondroitin sulfate in the present invention.

Mucopolysaccharides are extracellular components having one or two negatively charged groups per disaccharide repeating unit. Being a sulfated mucopolysaccharide, chondroitin sulfate carries an extra negative charge per repeating unit. Chondroitin sulfate has a $-2$ charge per unit (a carboxyl group and a sulfate group each supply one negative charge). The biological macromolecule of chondroitin sulfate forms a random coiled polymer, with the repulsive forces of the negative charges maintaining a minimum volume per molecule. The polyanion itself binds many water molecules so that it forms a mucopolysaccharide water composite and generates a protective cushion.

An intraocular lens, which is manufactured from a highly electrical insulating material, strongly attracts the endothelial layer of the cornea when direct tactile contact is made. There is, in fact, an actual transfer of the endothelial cellular network, as if there were an attraction of the layer by the lens. The highly electrically conductive chondroitin sulfate arrangement is eminently suitable to eliminate this electrical attractive force. The extra negative charge associated with chondroitin sulfate also endows it with greater molecular elasticity, making it an excellent lubricating material.

Since acid mucopolysaccharides are viscous, highly hydrated polyanions, showing a marked degree of interaction even in dilute solution, they impede the direct flow of fluids and thus contribute to the mechanical resistance to compression. The mucopolysaccharide will limit the flow of inflammatory products, for example, proteins.

Certain bacteria, for example, staphylococcus, contain hyaluronidase. An infection may spread by depolymerization, i.e. attack upon the mucopolysaccharide. Since chondroitin sulfate B does not respond to this enzyme, the use of chondroitin sulfate B would limit, or even eliminate, the activities of accidental infection during surgical procedures. Chondroitin sulfate also limits the movement of proteins and large molecules, thus aiding in the control of infection.

Chondroitin sulfate can play an active as well as a passive role. Thus, it can be utilized before, during and after trauma. As a passive instrument, chondroitin sulfate physically separates tissues and acts as a lubricant.

In an active role, chondroitin sulfate behaves as a molecular sieve. It collects large molecules that participate in adhesion formation and permits the smaller molecules to permeate through it. Thus there will be an exclusion of large molecules and a space exists along each chondroitin sulfate aggregate into which no protein can move. The sieving effect acts as a hindrance to the flow of various types of molecules based on the possible entanglement of the polysaccharide chains. This leads to the development of a three dimensional network. Thus large molecules are retarded in relation to their shape, electrical charge, polar groups, etc. In certain cases chondroitin sulfate sieving can be augmented by the addition of $Ca^{2+}$ ions.

Chondroitin sulfate itself is broken down as part of the healing process. The sulphur atom of chondroitin sulfate can be radioactively traced during its incorporation into healing tissue. Chondroitin sulfate diminishes tissue rejection in tissue implants, thus acting in an active role that serves various surgical procedures including those in ophthalmology.

Although both chondroitin sulfate and "HEALON", i.e., high molecular weight (polymerized) fraction of sodium hyaluronate available commercially from Pharmacia Labs, Inc., are mucopolysaccharides, these two substances are quite different. "HEALON" has a much higher molecular weight than chondroitin sulfate (the molecular weight of "HEALON" is greater than 1,000,000 as compared to about 50,000 to 100,000 for chondroitin sulfate). Chondroitin sulfate does not attain the great single chain lengths of "HEALON" molecules. Chondroitin sulfate has only about 50 repeating disaccharide units per chain as compated to more than about 15,000 units per chain for "HEALON".

After ophthalmic surgery, "HEALON" remains in the anterior chamber for a very long period of time, i.e., several days. Chondroitin sulfate, however, is completely dissipated after surgery within 24 to 36 hours.

The present invention involves the utilization of chondroitin sulfate as a protective agent prior to and/or during anticipated trauma, such as surgery, to minimize or eliminate cell damage. Chondroitin sulfate may also be administered during surgery to foster separation of tissue planes during surgical procedures including but not limited to general surgery, neurosurgery, orthopedic surgery, vascular surgery and gynecological surgery in protecting cells and maintaining body cavities and joint cavities and preventing adhesion formations.

The damage to cells during such surgery is generally of two kinds - mechanical and electrostatic. An exemplary protective coating for use during surgery would thus exhibit the following attributes: the ability to absorb the impact of mechanical contact, the ability to act as a good electrical conductor (to eliminate or reduce the electrostatic interaction between surgical instruments and the cells), high viscosity and biological compatibility. Chondroitin sulfate meets all these criteria.

All three isomer forms of chondroitin sulfate (A, B, and C) can be utilized in the present invention. Chondroitin sulfate A can be derived from whale cartilage; chondroitin sulfate B can be derived from porcine skin; and chondroitin sulfate C can be derived from shark cartilage. A fairly plentiful source for chondroitin sulfate is the nasal septa of cows. Chondroitin sulfate also exists in the trachea, aorta, tendons and other parts of the animal body. Certain sections of domesticated animal cartilage contain up to 40% chondroitin sulfate by weight. All forms of chondroitin sulfate with varying sulphur contents essentially have the same mechanism of protective action and would therefore be effective in the present invention.

Chondroitin sulfate isolated from shark cartilage, and designated as chondroitin sulfate D, has revealed an infrared spectrum identical with that of chondroitin sulfate C. However, the non-identity of the two polysaccharides as acceptors in enzymatic sulphation, and the unusually high sulphur content of chondroitin sulfate D (S, 7.6%; corresponding to 1.3 sulfate residues per hexosamine) suggests that they might be distinct species. Chondroitin sulfates from shark preparations manifest excellent properties in anterior segment surgery.

Chondroitin sulfate may be utilized in the present invention in various forms and concentrations depending upon the particular tissue area and method of application. One of ordinary skill in the art can readily determine with a minimum amount of experimentation the appropriate amount of chondroitin sulfate to be applied depending on such factors as desired viscosity or coating thickness, whether the chondroitin sulfate is to be applied topically or injected, etc. The concentration of chondroitin sulfate to be used in solutions depends also upon whether the chondroitin sulfate is to be used in vivo as a protective agent or in vitro as a storage and preserving solution.

In the case of in vivo protective solutions, it is preferred that the chondroitin sulfate be present as a component in the physiological solutions in amounts of about 40 to 55 weight percent of the solution, and more preferably about 50 to 55 weight percent of the solution. Concentrations below about 40% by weight may still be satisfactory, but not as effective as the preferred concentrations indicated above. For example, as described in our U.S. Pat. No. 4,486,416 a 20 weight percent solution of chondroitin sulfate was satisfactory for in vivo cataract extractions with rabbits and monkeys. Concentrations above about 60% may also be effective, but are not preferred since higher concentrations will begin to dehydrate tissues to which the chondroitin sulfate is applied.

In the case of in vitro preservative solutions, concentrations of about one to twenty weight percent of chondroitin sulfate are preferred, and more particularly about one to five weight percent chondroitin sulfate.

The solutions are preferably aqueous solutions which in addition to chondroitin sulfate may be substantially composed of normal saline solution, basic salt solution or other buffered solutions which are commonly known and used in handling biological materials. Some of these physiological solution bases and other additives are exemplified more fully below for particular applications, and others will be apparent to those of ordinary skill in the art. A particularly preferred solution for use in in vivo applications of the present invention comprises 50% by weight (400mg/ml) chondroitin sulfate in a disodium phosphate (14mg/ml)/monosodium phosphate hydrate (0.13mg/ml) buffer.

The chondroitin sulfate solution can be introduced to the anticipated area of the surgery or treatment area by any convenient means such as using a cannula or needle, i.e., injected into a body cavity, joint or vessel, or using irrigating devices or swabs for topical application.

Protection of Cells and Tissues of Internal Body Tissues, Organs and Cavities

During any invasive procedure, such as surgery, the cells of the coverings and linings of various body organs, tissues and cavities are subject to trauma from the surgical cutting as well as other manipulations which may be performed during the invasive procedure. These body linings and coverings are covered with endothelial, mesothelial or epithelial cells. The protection of endothelial cells of the cornea-has already, been discussed in some detail in our U.S. Pat. No. 4,486,416. Ser. No. 239,79. Endothelial cells also cover the inside of other body organs such as blood vessels. Mesothelial cells are the flat squamous cells which cover the intestines and the true serous membranes of the body cavity including the peritoneum, the pleural cavity and the pericardium. While epithelial cells are primarily found covering the outside surfaces of the body, they also line the esophagus and the inside of the mouth.

The use of chondroitin sulfate to protect cells which cover the internal body coverings and linings according to the present invention is particularly advantageous during invasive procedures such as surgery, and may be used in irrigating solutions in place of or as an additive to conventional irrigating solutions such as normal saline or Ringer's solution to flush tissue surfaces during surgery. The prophylactic effect of chondroitin sulfate in abdominal surgical procedures is demonstrated by the following experiments:

Sprague Dawley white rats were anesthetized intraperitoneally with sodium pentobarbital, and a celiotomy was performed by removing a strip of skin using scissors and similarly opening the linea alba. A loop of intestine from the rats was delivered onto a polypropylene apron which was attached to the belly of the rats with towel clamps and moistened with buffered mammalian Ringer's solutions (BRS). The loop of intestine was also moistened with BRS and kept moist throughout the experiment. Care was taken that the portion of the gut being investigated was not a part actually contacted by fingers or surgical instruments. At the end of an experiment each rat was sacrificed by intracardiac injection of strong pentobarbital solution.

A series of experiments was performed on the exposed loop of intestine of each rat with washing, abrading, staining and application of chondroitin sulfate in various orders of performance, with one or more of these steps being omitted for comparison. The abrasion was done with a Halda force gauge with a curved wire tip. To the extent possible, an abrasion consisted of 15 strokes of the tip against the side of the intestine throughout a longitudinal distance of 1 cm such that the needle of the gauge remained between 10 and 15 grams for 90% of each stroke. The abrasion was applied along the long axis of the intestine, and the mesentery was not abraded due to the tendency of the staining dye to leak under the loop of gut so as to be inaccessable to washing and give the false appearance of staining. The staining consisted of applying at least 1 ml of the purple stain, Acid Violet TFH (more was applied if the first application did not cover the area), and the stain was allowed to remain for at least twenty seconds and not more than about 45 seconds. Washing or flushing was done by copious rinsing with BRS (at least 25 ml per site from the open end of an intravenous infusion tube). In final washes after staining, enough BRS was used until the fluid .pa draining away from the area of staining was uncolored to visual examination (usually 25–100 ml but as much as 300 ml).

The chondroitin sulfate solution used was a 50 weight percent chondroitin sulfate solution in phosphate buffer as described above. In the results described below "random staining" refers to the appearance of areas that took the stain (generally very lightly) in a manner unrelated to the experimental manipulations and with no recognizable borders or edges to the stained part. This may be due to handling and/or drying of the tissues. "Distinct staining" refers to areas having recognizable edges and rather uniform depth of staining. Five series of experiments with five or six rats each were performed as described below with the indicated results:

Series No. 1 (Average weights of rats = 140 gm)

1. One ml CDS intraperitoneally before celiotomy; washed copiously after opening; abraded; stained; washed. Visual appearance: deep distinct staining of abraded area and
2. One ml CDS intraperitoneally before celiotomy; abraded; stained; washed copiously (did not wash after opening). Visual appearance: very lightly stained.
3. One ml CDS intraperitoneally. Died.
4. CDS locally after opening and washing; no abrasion; stained; washed. Visual appearance: very little and very light staining.
5. No CDS; opened; washed; abraded; stained; washed. Visual appearance: deep discrete staining at place of abrasion; some light "random staining".

Series No. 2 (Average weight of rats = 165 gm)

1. One ml CDS intraperitoneally; wash; no abrasion; stain; wash. Visual appearance: no staining.
2. One ml CDS intraperitoneally; abrade; flush; stain; flush. Visual appearance: no staining.
3. One ml CDS intraperitoneally; flush first; abrade; flush; stain; flush. Visual appearance: distinct staining.
4. Two drops CDS locally after opening on left; abrade on both sides; flush; stain; flush. Visual appearance: CDS part much less staining than non-CDS, some "random" staining.
5. Two drops CDS locally on right after abrading; flush; stain; flush. Visual appearance: both sides stained, some "random" staining.

Series No. 3 (Average weight of rats = 200 gm)

1. Flushed; Two drops of CDS on left; abraded both sides; washed; stained; washed. Visual appearance: slight stain on left (CDS), no stain on right (no CDS).
2. Flushed; Two drops of CDS on left; abraded both sides; washed; stained; washed. Visual appearance: no stain on left (CDS), stained on right (no CDS).
3. No flush on opening; Two drops CDS on right; abraded both sides; washed; stained; washed. Visual appearance: light stain on right (CDS), heavy distinct stain on left (no CDS).
4. Flush; Two drops CDS locally on right; abrade both sides; wash; stain; wash. Visual appearance: right side (CDS) no stain, left side (no CDS) heavy distinct stain.
5. Woke up.

Series No. 4 (Average weight of rats = 250 gm)

All had sequence of: wash; apply CDS (two drops) locally to one part; abrade both sides; wash; stain; wash.
1. CDS on right. Visual appearance: some random staining, CDS part much less than non CDS part.
2. CDS on left. Visual appearance: left side (CDS) no stain, right side (no CDS) deep stair
3. CDS on right. Visual appearance: right side (CDS) no stain, left side (no CDS) moderate but distinct staining.
4. CDS on left. Visual appearance: left side (CDS) no stain, right side (no CDS) deep staining.
5. Woke up, given more pentobarbital but still awake, died later.

Series No. 5 (Average weight of rats = 250 gm)

1. (Control) wash; (no abrasion, no CDS) stain; wash. Visual appearance: slight random staining.
2. Wash; abrasion on left only; (no. CDS) wash; stain; wash; Visual appearance: clear distinct staining of abraded part, light random staining.
3. (No wash) Two drops CDS locally on right; wash; stain. Visual appearance: random staining on CDS part, distinct staining on non CDS part.
4. Wash, Two drops CDS locally on left; abrade both sides; wash; stain; wash. Visual appearance: left side (CDS) light stain, right side (no CDS) heavy distinct stain.
5. Wash; two drops CDS locally on right; abrade both; wash; stain; wash. Visual appearance: right side (CDS) random staining, left side (no CDS) distinct staining.
6. Wash; two drops CDS locally on left; abrade left (CDS part only); wash; stain; wash. Visual appearance: left side (CDS) no stain, right side (no CDS, no abrasion) random staining.

Application of the chondroitin sulfate (CDS) preparation either locally or intraperitoneally, before abrasion of the visceral mesenteric surface, in all sixteen rats tested prevented or significantly decreased the staining of abraded areas by the Acid Violet dye, thus supporting the hypothesis that CDS prevents or moderates the exfoliation or destruction of cells from the visceral mesenteric surface.

Chondroitin Sulphate in Storage Solutions

Various media have been prepared to successfully preserve animal tissues for storage and/or transportation for later use. However, even with such specially prepared storage media, the practical, useful storage life is limited to a few days. For example, MK medium (See McCarey, BE and Kaufman, HE, "Improved Corneal Storage", Investigational Ophthalmology 13:165 (1974) has been shown to successfully preserve corneal tissue of rabbits for as long as fourteen days but subsequent studies (see Kaufman, H. E. et al. 'Chondroitin Sulfate in a New Cornea Preservation Medium,' American Journal of Ophthalmology, 98:112 (1984)) indicated that in practice the MK medium could preserve corneal tissue in storage only for up to four days, whereas it would be desirable to be able to store corneal tissue in a refrigerator with no additional processing for at least two weeks.

It has been found that the addition of chondroitin sulfate in amounts of about 1 to 20, and preferably about 1 to 5 weight percent to conventional or special storage media will significantly extend the storage capabilities of the media up to several weeks. A particularly preferred aqueous solution contains 2.5% CDS in 0.02M HEPES, TC 199 for osmolarity, sodium bicarbonate and gentamicin sulfate. It will be understood that chondroitin sulfate alone, or a buffered solution of chondroitin sulfate alone will not suffice as a storage media, since it is necessary to include the metal ions and other nutrients needed by the viable tissue. The ability of chondroitin sulfate to extend the storage capacity of animal tissues in storage media is illustrated by the following experiments performed following our suggestions:

The solutions which were used as test media with or without chondroitin sulfate (CDS) included BSS (basic salt solution), BSS Plus (a commercially available long term (1-6 hours) irrigating solution), MEM (minimal essential medium), TC 199 (a standard commercially available tissue culture medium), HEPES (a standard commercially available cell culture buffer system), FLUOSOL (a blood substitute available from The Green Cross Corporation), AMVISC (a 1% sodium hyaluronate in BSS commercially available from Medchem and Precision Cosmet), Hanks BSS (a commercially available tissue culture medium) without phenol red indicator, HEALON, and dextran of different molecular weights. All test solutions contained 200 ug/ml gentamicin sulfate. Low molecular weight components of chondroitin sulfate were removed for the sake of uniformity.

Human corneas initially perserved in MK (McCarey-Kaufman) medium for one to three days or whole globes stored in moist chambers for one to three days were stored in the experimental media for two weeks. Viability of the endothelial cells was assessed morphologically by trypan blue staining. Some corneas were examined by electron microscopy. The results are shown in Table I.

The solutions containing 2.5% to 10% chondroitin sulfate, TC199 and HEPES buffer yielded the most satisfactory results. Grafts stored in a medium containing either 2.5% or 5% chondroitin sulfate displayed minimal trypan blue staining and normal structure by electron microscopic analysis. Subsequently, such corneas have been used in animal eyes and in five human eyes with satisfactory results in terms of clarity.

TABLE I

Analysis of Corneas and Globes Preserved for 14 Days at Refrigerator Temperature (4 C.) in Various Media

| Composition of Medium | No. Tested Globes | No. Tested Corneas | Days from Death of Donor to Beginning of Study Globes | Days from Death of Donor to Beginning of Study Corneas | Gross Appearance After 14-day Storage in Experimental Medium | Endothelial Cells Stained With Trypan Blue (%) |
|---|---|---|---|---|---|---|
| TC 199, HEPES, 2.5% CDS | 1 | 1 | 2 | 2 | Clear | 0 to 1 |
| TC 199, HEPES, 10% CDS | 1 | 1 | 1 | 4 | Clear to slightly cloudy | 5 |
| TC 199, HEPES, 1% CDS | 3 | 6 | 2 to 3 | 2 to 3 | Clear to slightly cloudy | 60 |
| TC 199, HEPES, dextran | 3 | 5 | 1 to 3 | 2 to 4 | Slightly cloudy to cloudy | 60 |
| BSS, glucose, HEPES, 10% CDS | 0 | 2 | — | 2 to 3 | Clear | 0 |
| BSS, glucose, HEPES, 1% CDS | 2 | 4 | 3 | 1 to 3 | Clear to Cloudy | 50 |
| BSS, glucose, HEPES, dextran | 2 | 5 | 2 to 3 | 1 to 3 | Clear to cloudy | 60 |
| TC 199, 20% CDS | 4 | 2 | 1 to 2 | 2 to 3 | Clear | 0 to 1 |
| TC 199, 10% CDS | 5 | 3 | 0.25 to 2 | 2 to 3 | Clear to slightly cloudy | 16 |
| TC 199, 5% CDS | 1 | 1 | 2 | 1 | Clear to slightly cloudy | 50 |
| TC 199, 2% CDS | 1 | 1 | 2 | 2 | Slightly to medium cloudy | 50 |
| BSS, 10% CDS | 1 | 1 | 3 | 3 to 4 | Cloudy | 100 |
| BSS, 5% CDS | 1 | 2 | 1 | 3 | Cloudy | 0# |
| BSS, 2% CDS | 2 | 1 | 1 to 3 | 3 | Cloudy | 0# |
| BSS Plus, 20% CDS | 2 | 0 | 1 to 2 | — | Clear | ND+ |
| BSS Plus, 10% CDS | 2 | 0 | 0.25 to 2 | — | Cloudy | 50 |
| BSS Plus, 5% CDS | 2 | 0 | 1 to 2 | — | Cloudy | 45 |
| BSS Plus, 2% CDS | 1 | 1 | 2 | 3 | Clear to Cloudy | 95 |
| TC 199, 0.2% fat-free albumin | 1 | 2 | 2 | 1 to 2 | Cloudy to clear | 50 |
| MEM, 0.2% fat-free albumin | 1 | 1 | 2 | 1 | Clear to slightly cloudy | 65 |
| MEM, 20% CDS | 1 | 0 | 1 | — | — | 30 |
| MEM, 10% CDS | 1 | 1 | 1 | 4 | Slightly cloudy to cloudy | 65 |
| Fluosol | 0 | 1 | — | 3 | — | 30 |
| TC 199, 50% Amvisc | 2 | 0 | 2 | — | Slightly cloudy to cloudy | 50 |
| TC 199, 50% Healon | 1 | 0 | 2 | — | Slightly cloudy to cloudy | 50 |
| TC 199*, 50% Healon | 1 | 0 | 2 | — | Cloudy | 0# |
| M-K medium | 1 | 0 | 2 | — | Slightly cloudy | 100 |
| Modified M-K medium | 0 | 2 | — | 0.33 to 2 | Cloudy to slightly cloudy | 50 |

No endothelium.
+Not done; tissue used as graft in monkey eye;
*Double strength.

One patient who received a graft that had been stored in the experimental medium for twelve days demonstrated a complete endothelial sheet and an endothelial cell density of 1800 cells/mm two weeks after surgery. Patients receiving transplants stored 14 and 16 days also had normal postoperative graft thickness.

Chondroitin Sulfate Treatment of Aseptic Inflammation of Animal Joints Aseptic inflammation (i.e., without infection by microorganisms) of the joints of animals, particularly four-legged animals such as horses, is a serious characteristic of degenerative joint disease. As the cartilage cells of the joint degenerate, the synovial fluid (which is largely hyaluronic acid) of the joint is of such inferior quality that it has very poor lubricating capacity (i.e., it becomes nonviscous), so that inflammation of the joint results.

It has been found that the injection of effective amounts of chondroitin sulfate, which is a significant component of the articular cartilage, into the inflamed joint reduces inflammation and prevents further degeneration of the cartilage (mainly through protection of cells in the joint cavity and also through lubrication and cushioning effects) and possibly causes some regeneration of cartilage through stimulation of mucopolysaccharide synthesis by the chondrocytes. That is, the chondroitin sulfate provides a protective effect against further cartilage damage, with possibly the mechanical and/or hydrodynamic potentiation of healing or regenerative effects.

Chondroitin sulfate may be injected intraarticularly in generally the same types of vehicles (physiologic solutions) as described above for surgery and other in vivo cell protection, preferably at concentrations of about 40 to 55 weight percent. The amount of solution to be injected varies depending upon the particular joint and joint size being treated. As an example, about 4 cc of a 50 weight percent solution is satisfactory for a horse leg joint.

While chondroitin sulfate has found to be particularly advantageous in the treatment of the hock, knee and fetlock joints of horses, it is believed that chondroitin sulfate broader application in treating the leg joints of other animals including those of humans and larger dogs, cattle, etc. having similar joint problems. For example, chondroitin sulfate may be useful in treating arthritic joints and other degenerative joint conditions in humans and other animals. The effectiveness of chondroitin sulfate in treating equine joints is demonstrated by the following experiments:

Forty-six standardbred horses with no more than one affected joint at a time were included in the study. None of the horses had fractures and none had received other intraarticular therapy in the affected joint within the previous four weeks. Of the total of 54 joints treated during the study, 45 joints were treated with a 50 weight percent chondroitin sulfate solution with phosphate buffer as indicated above (hereinafter referred to as CDS or the CDS therapy), and 9 joints were treated with the commercially available "HYLARTIL VET," (an equine product similar to "HEALON" available from Pharmcia Labs, Inc. comprising 1% sodium hyaluronate).

Prior to treatment, joint temperature and lameness were measured and recorded. A sample of synovial fluid was removed from the test joint and replaced with an equal volume of the treatment solution of 4 ml. being careful to avoid extensive "overfilling" of the joint. Temperature and lameness were evaluated at one and two weeks after treatment. If the joint condition was considered to be 50% or less improved, then a second administration of the test solution was made equal to the first, and temperature and lameness were again evaluated weekly.

Analysis of synovial fluid revealed no consistent correlation with clinical results. However, joint temperature, stride and race test results correlated well with clinical observations. Table II shows the mean temperature differences for inflamed joints minus control joints prior to and after treatment. Joint temperatures prior to treatment were on the average 3.6 degrees C higher than those of the opposite control joint. Overall, the 45 joints treated with CDS showed improvement of 74.2% and 85.3% one and two weeks respectively after therapy, while the HYLARTIL VET therapy in 9 joints showed improvement of 71.5% and 82.8% one and two weeks, respectively after therapy.

Since the horse favors the affected limb and places the least amount of weight possible for the shortest possible time on that limb, there appears to be a difference between the length of stride made by the anterior limb versus the posterior limb. With severely affected joints, the anterior limb stride is longer than the posterior limb stride, but as the inflammation subsides, the anterior stride shortens and the posterior stride lengthens with modest change in the sum of the stride lengths. The stride lengths of the anterior limb and the posterior limb approach equality as recovery to soundness is achieved, and the sum of stride lengths may increase as soundness of all limbs is achieved.

As shown in Table III, the stride length decreased for anterior limbs and increased for posterior limbs after therapy with either CDS or HYLARTIL VET. Both treatments resulted in improvement of the stride in the horse favoring an affected limb, and, in fact, the CDS therapy showed a slight increase in the sum of the stride length, suggesting return to soundness of the limbs.

Actual racetrack performances of 25 horses treated with CDS and 5 treated with HYLARTIL VET were obtained and compared before and after therapy. All but 5 of the CDS treated horses showed improvement in performance (decrease in elapsed time to complete the race), while 3 of the 5 HYLARTIL VET treated horses showed improvement. Table IV shows the performance data of these horses. CDS treated horses improved by decreasing their elapsed race time by an average of 2.2 seconds, while the HYLARTIL VET treated horses decreased elapsed race time by 0.8 seconds.

The results of the foregoing tests correlated well with clinical evaluations which showed clinical improvement as joint inflammation subsided and the joint returned to soundness. The results of the study suggest that CDS therapy is equally effective, if not more so, as HALARTIL VET for indications of aseptic inflammation in the equine joint.

TABLE II

| | EQUINE JOINT TEMPERATURE | | | | | |
|---|---|---|---|---|---|---|
| | CDS THERAPY | | | HYLARTIL VET THERAPY | | |
| JOINT | Pretherapy | 1 wk | 2 wk | Pretherapy | 1 wk | 2 wk |
| knee | N = 16 3.5 C | 1.2 C (66%) | 1.1 C (69%) | N = 5 3.0 C (80%) | 0.6 C | 0.2 C (93%) |
| Front fetlock | N = 27 3.6 | 0.7 (81%) | 0.3 (92%) | N = 2 4.5 | 2.0 (56%) | 1.5 (67%) |
| Hind Fetlock | N = 1 0.0 | 0.0 | 0.0 | N = 1 9.0 | 3.0 (66%) | 2.0 (78%) |
| Hock | N = 11 4.0 | 0.7 (83%) | 0.0 (100%) | N = 1 2.0 | 0.0 (100%) | 0.0 (100%) |
| All Joints | N = 45 3.6 | 0.93 (74.2%) | 0.53 (85.3%) | N = 9 3.9 | 1.11 (71.5%) | 0.67 (82.8%) |
| SEM = | +/− 0.52 | +/− 0.25 | +/− 0.26 | +/− 1.23 | 0.39 | 0.29 |

The data of this table represent the mean values of the temperature difference between the inflamed joint and the control joint. N = number of joints evaluated. SEM is the standard error of the mean.

TABLE III

STRIDE TEST ANALYSIS
(Change in Stride Length -inches- After Therapy)

| INJURED JOINT | CDS THERAPY | | HYLARTIL VET THERAPY |
|---|---|---|---|
| KNEE | ANT. −0.63 +/− 0.51 inches | | ANT. 0.40 +/−0.60 inches |
|  | POST. 1.0 +/− 0.40 | | POST. 0.00 +/− 0.32 |
| N = 16 | SUM 0.37 +/− 0.34 | N = 5 | SUM 0.40 +/− 0.68 |
| FRONT | ANT. −1.94 +/− 0.74 | | ANT. −1.0 +/− 1.0 |
| FETLOCK | POST. 2.06 +/− 0.78 | | POST. 1.0 +/− 1.0 |
| N = 27 | SUM 0.12 +/− 0.19 | N = 2 | SUM 0.0 +/− 0.0 |
| HIND | ANT. 0.0 | | ANT. −5.0 +/− 0.0 |
| FETLOCK | POST. 1.0 | | POST. 5.0 +/− 0.0 |
| N = 11 | SUM 1.0 +/− 1.0 | N = 1 | SUM 0.0 +/− 0.0 |
| HOCK | ANT. −3.0 +/− 1.10 | | ANT. −1.0 +/− 1.0 |
|  | POST. 3.0 +/− 1.10 | | POST. 0.0 +/− 0.0 |
| N = 1 | SUM 0.0 +/− 0.47 | N = 1 | SUM −1.0 +/− 1.0 |

TABLE IV

IMPROVEMENT OF RACETRACK PERFORMANCE

| CDS THERAPY | | HYLARTIL VET THERAPY | |
|---|---|---|---|
| HORSE | RACE TIME CHANGE (SEC) | HORSE | RACE TIME CHANGE (SEC) |
| AU | −5 | AS | 0 |
| BN | −2 | KLM | +1 |
| BA | −3 | MBC | −2 |
| BL | −1 | MBF | 0 |
| CM | −1 | WD | −3 |
| CL | −2 | | |
| CR | −2 | | |
| CS | −4 | N = 5 M = −0.8 | |
| FL | −3 | SD = 1.47 | |
| CGA | 0 | SEM = 0.74 | |
| GS | −1 | | |
| GS | −1 | | |
| GS | −2 | | |
| LD | −4 | | |
| MEN | −4 | | |
| NN | +2 | | |
| PN | −5 | | |
| PP | 0 | | |
| RW | −2 | | |
| SS | −3 | | |
| SD | −2 | | |
| SB | +1 | | |
| TO | −5 | | |
| TTB | +4 | | |
| TTB | −10 | | |

N = 25 M = −2.2
SD = 2.67
SEM = 0.55

The values in this table are drived from registered track records of each horse. The change in time represents the time of succeeding races after treatment minus the time of the race preceeding therapy. All times were registered within one to two weeks prior to therapy and three to four weeks after therapy.

It will be recognized by those skilled in the art that changes may be made to the above-described embodiments of the invention without departing from the broad inventive concepts thereof. It is understood, therefore, that this invention is not limited to the particular embodiments disclosed, but it is intended to cover all modifications which are within the scope and spirit of the invention as defined by the appended claims.

We claim:

1. A method of protecting the cells of the linings and coverings of internal human and animal tissues, organs and body cavities subject to exposure to surgical trauma, which comprises administering a prophylactically effective amount of chondroitin sulfate directly to said cells such that chondroitin sulfate is present on said cells during said exposure of said cells to said trauma.

2. A method according to claim 1 which further comprises administering chondroitin sulfate to said cells after said exposure to said trauma.

3. The method of claim 1 wherein said chondroitin sulfate is selected from the group consisting of chondroitin sulfate A, chondroitin sulfate B and chondroitin sulfate C.

4. A method according to claim 1 wherein said chondroitin sulfate is topically administered.

5. A method according to claim 1 wherein said chondroitin sulfate is injected into a body cavity or vessel.

6. A method according to claim 1 wherein said chondroitin sulfate is administered as a component of a physiological solution.

7. A method according to claim 6 wherein said solution comprises about 40 to 55 weight percent chondroitin sulfate.

8. A method according to claim 1 which comprises administering chondroitin sulfate prior to said exposure to trauma.

9. The method according to claim 1 which comprises administering chondroitin sulfate during said trauma.

10. A method according to claim 1 wherein chondroitin sulfate is administered as a surgical irrigating solution.

11. A method according to claim 1 wherein said cells are selected from the group consisting of endothelial, mesothelial and epithelial cells.

* * * * *